(12) United States Patent
Giles et al.

(10) Patent No.: US 8,409,554 B2
(45) Date of Patent: Apr. 2, 2013

(54) HAIR TREATMENT COMPOSITIONS

(75) Inventors: Colin Christopher David Giles, Bangkok (TH); Artit Kijchotipisarn, Bangkok (TH); Anuchai Sinsawat, Bangkok (TH)

(73) Assignee: Conopco, Inc., Englewood Cliffs, NJ (US)

( * ) Notice: Subject to any disclaimer, the term of this patent is extended or adjusted under 35 U.S.C. 154(b) by 1195 days.

(21) Appl. No.: 10/592,921

(22) PCT Filed: Feb. 10, 2005

(86) PCT No.: PCT/EP2005/001454
§ 371 (c)(1), (2), (4) Date: Sep. 14, 2006

(87) PCT Pub. No.: WO2005/089702
PCT Pub. Date: Sep. 29, 2005

(65) Prior Publication Data
US 2008/0233070 A1   Sep. 25, 2008

(30) Foreign Application Priority Data
Mar. 17, 2004 (EP) .................... 04251506

(51) Int. Cl.
*A61Q 5/12* (2006.01)

(52) U.S. Cl. ............... 424/70.28; 424/70.1; 424/70.27

(58) Field of Classification Search ............. 424/401
See application file for complete search history.

(56) References Cited

U.S. PATENT DOCUMENTS

| | | | | |
|---|---|---|---|---|
| 4,102,795 A | * | 7/1978 | Minegishi et al. | 424/70.19 |
| 2002/0136771 A1 | * | 9/2002 | Parr et al. | 424/488 |
| 2003/0186834 A1 | * | 10/2003 | Pereira et al. | 510/499 |
| 2003/0190302 A1 | * | 10/2003 | Frantz et al. | 424/70.24 |
| 2004/0092415 A1 | * | 5/2004 | Focht et al. | 510/130 |
| 2004/0115159 A1 | * | 6/2004 | Tadlock et al. | 424/70.22 |

FOREIGN PATENT DOCUMENTS

| | | |
|---|---|---|
| EP | 0 234 475 | 9/1987 |
| WO | 03/060046 | 7/2003 |

OTHER PUBLICATIONS

Luviquat Information Sheet, Oct. 1993, available at: www.basf-korea.co.kr/02_products/04_finechemicals/document/cosmetic/tech/conditioning/down.asp?file=luviquatmonocp.pdf.*
Kids Health. Skin, Hair and Nails, 2011.*
Dow Corning 1785 emulsion (Nov. 7, 2012).*
Natrosol, hydroxyethylcellulose (Nov. 7, 2012).*
Dow Corning 245 fluid (Nov. 7, 2012).*

* cited by examiner

*Primary Examiner* — Jyothsna Venkat
(74) *Attorney, Agent, or Firm* — Ronald A. Koatz

(57) ABSTRACT

Aqueous hair treatment compositions which comprise a mono $C_{14}$-$C_{22}$ trimethylammonium surfactant, a di-($C_{20}$-$C_{24}$) imidazoline quaternary surfactant, and a mono $C_{12}$-$C_{22}$ alkyl hydroxyethyl dimethylammonium surfactant provide improved hair conditioning benefits.

5 Claims, No Drawings

HAIR TREATMENT COMPOSITIONS

FIELD OF THE INVENTION

The invention is concerned with hair treatment compositions, particularly conditioner compositions.

BACKGROUND AND PRIOR ART

The surface of the hair fibre is an important attribute relating to the overall appearance and feel of the hair. The present invention relates to hair conditioners which are applied to the hair to improve hair fibre surface properties such as smoothness, softness, manageability, cuticle integrity, anti-static and shine.

WO 03/060046 discloses compositions that include mixtures of dialkyl imidazoline quats and monoalkyl ammonium quats for personal care and cosmetic products.

The present inventors have found that specific combinations of cationic surfactants can be found to give the conditioning properties referred to above. Furthermore these properties are maintained even at low levels of the cationic surfactants in question.

DESCRIPTION OF THE INVENTION

In a first aspect, the invention provides a hair treatment composition comprising:
a) from 0.2 to 5% by weight of the total composition of a cationic surfactant according to the formula: $[N(CH_3)_3(R_1)]^+ (X)^-$ wherein $R_1$ is a $C_{14}$ to $C_{22}$ alkyl group and X is a salt-forming anion selected from halogen, acetate, citrate, lactate, glycolate, nitrate, sulphate, and methosulphate radicals;
b) from 0.01 to 1.0% by weight of the total composition of a di-($C_{20}$-$C_{24}$) imidazoline quaternary surfactant; and
c) from 0.0001 to 0.5% by weight of the total composition of a cationic surfactant according to the formula $[N(CH_3)_2(CH_2CH_2OH)R_2]^+Y^-$ wherein $R_2$ is a $C_{12}$-$C_{22}$ alkyl group and Y is a salt-forming anion selected from halogen, acetate, citrate, lactate, glycolate, phosphate, nitrate, sulphate, and methosulphate radicals.

The invention also encompasses the application of such compositions to the hair and/or scalp and the use of the compositions to improve the condition of the hair.

DETAILED DESCRIPTION OF THE INVENTION

Hair treatment compositions according to the invention may suitably take the form of leave-on or rinse-off conditioners, sprays, mousses or lotions.

Conditioner Compositions

Compositions in accordance with the invention are preferably formulated as conditioners for the treatment of hair (typically after shampooing) and subsequent rinsing. Preferably, the compositions are applied to the hair and then the hair is rinsed with water (so-called rinse-off compositions).

Alkyl Trimethylammonium Cationic Surfactant

Compositions according to the invention contain from 0.2 to 5% by weight of the total composition, preferably 0.3 to 5%, more preferably 0.5 to 2%, most preferably 0.6 to 1.5% by weight of a cationic surfactant according to the formula: $[[N(CH_3)_3(R_1)]^+ (X)^-$ wherein $R_1$ is a $C_{14}$ to $C_{22}$ alkyl group and X is a salt-forming anion selected from halogen, acetate, citrate, lactate, glycolate, phosphate, nitrate, sulphate, and methosulphate radicals. Preferably the anion is a methosulphate radical or a halogen, in particular chloride.

$R_1$ is preferably an $C_{16}$, $C_{18}$ or $C_{22}$ alkyl group.

Particularly preferred are cetrimonium chloride, and cetrimonium methosulphate and in particular mixtures of these two cationic surfactants.

Dialkyl Imidazoline Quaternary Surfactant

Compositions of the invention comprise from 0.01 to 1.0% by weight of the total composition, preferably from 0.05 to 0.5%, preferably from 0.1 to 0.4%, most preferably from 0.2 to 0.4% by weight of a dialkyl imidazoline quaternary surfactant, where the alkyl groups are independently selected from $C_{20}$ to $C_{24}$ alkyl chains. Preferably both of the alkyl groups of the dialkyl imidazoline quaternary surfactant have the same chain length. Suitable dialkyl imidazoline quaternary surfactants and methods of their manufacture are described in the published patent application WO 03/060046. The anion forming part of the dialkyl imidazoline quaternary surfactant is a salt-forming. anion selected from halogen, acetate, citrate, lactate, glycolate, phosphate, nitrate, sulphate, and methosulphate radicals. Particularly preferred is dibehenyl imidazoline quat (having the CTFA designation Quaternium-91).

Alkyl Hydroxyethyl Dimethylammonium Surfactant

Compositions according to the invention also comprise from 0.0001 to 0.5% by weight of the total composition, preferably from 0.001 to 0.2%, more preferably 0.01 to 0.1%, most preferably 0.015 to 0.05% by weight of an alkyl hydroxyethyl dimethylammonium cationic surfactant according to the formula $[N(CH_3)_2(CH_2CH_2OH)R_2]^+Y^-$ where $R_2$ is a $C_{12}$ to $C_{22}$ alkyl: group and Y is a salt-forming anion selected from halogen, acetate, citrate, lactate, glycolate, phosphate, nitrate, sulphate, and methosulphate radicals. Preferably, Y is phosphate. A preferred alkyl hydroxyethyl dimethylammonium surfactant is hydroxyethyl cetyldimonium phosphate (available commercially as LUVIQUAT mono CP ex BASP).

Fatty Material

Conditioner compositions of the invention comprise from 1 to 10% by weight of a fatty material. The combined use of fatty materials and cationic surfactants in conditioning compositions is believed to be especially advantageous, because this leads to the formation of a lamellar phase, in which the cationic surfactant is dispersed.

By "fatty material" is meant a fatty alcohol, an alkoxylated fatty alcohol, a fatty acid or a mixture thereof.

Preferably, the alkyl chain of the fatty material is full saturated.

Representative fatty materials comprise from 8 to 22 carbon atoms, more preferably 16 to 22. Examples of suitable fatty alcohols include cetyl alcohol, stearyl alcohol and mixtures thereof. The use of these materials is also advantageous in that they contribute to the overall conditioning-properties of compositions of the invention.

Alkoxylated, (e.g. ethoxylated or propoxylated) fatty alcohols having from about 12 to about 18 carbon atoms in the alkyl chain can be used in place of, or in addition to, the fatty alcohols themselves. Suitable examples include ethylene glycol cetyl ether, polyoxyethylene (2) stearyl ether, polyoxyethylene (4) cetyl ether, and mixtures thereof.

The level of fatty alcohol material in conditioners of the invention is suitably from 1 to 10, preferably from 1.5 to 8 and more preferably from 2 to 6 percent by weight of the composition. The weight ratio of fatty material to total level of quaternary cationic surfactant is preferably from 2:1 to 12:1, more preferably from 2.5:1 to 6:1, most preferably from 3:1 to 6:1

Aqueous Composition

Compositions according to the invention are preferably aqueous compositions, meaning that they preferably comprise greater than 50% by weight of water, more preferably more than 60%, most preferably more than 70%.

Conditioning Oil

A preferred further component of compositions according to the invention is hydrophobic conditioning oil. In order for such an oil to exist in the preferred form as discrete droplets in the compositions according to the invention, it must be water-insoluble. By water-insoluble is meant that the solubility in water at 25° C. is 0.01% by weight or less.

It is preferred if the conditioning oil is non-volatile, by which it is meant that the vapour pressure of the oil at 25° C. is less than 10 Pa.

As used herein, the term "conditioning oil" includes any material, which is used to give a particular conditioning benefit to hair. For example, suitable materials are those, which deliver one or more benefits relating to shine, softness, combability, wet-handling, anti-static properties, and protection against damage, body, volume, stylability and manageability.

Suitable hydrophobic conditioning oils are selected from hydrocarbon oils, fatty esters, silicone oils and mixtures thereof.

Hydrocarbon oils include cyclic hydrocarbons, straight chain aliphatic hydrocarbons (saturated or unsaturated), and branched chain aliphatic hydrocarbons (saturated or unsaturated). Straight chain hydrocarbon oils will preferably contain from about 12 to about 30 carbon atoms. Branched chain hydrocarbon oils can and typically may contain higher numbers of carbon atoms. Also suitable are polymeric hydrocarbons of alkenyl monomers, such as $C_2$-$C_6$ alkenyl monomers. These polymers can be straight or branched chain polymers. The straight chain polymers will typically be relatively short in length, having a total number of carbon atoms as described above for straight chain hydrocarbons in general. The branched chain polymers can have substantially higher chain length. The number average molecular weight of such materials can vary widely, but will typically be up to about 2000, preferably from about 200 to about 1000, more preferably from about 300 to about 600.

Specific examples of suitable hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used. Exemplary branched-chain isomers are highly branched saturated or unsaturated alkanes, such as the permethyl-substituted isomers, e.g., the permethyl-substituted isomers of hexadecane and eicosane, such as 2, 2, 4, 4, 6, 6, 8, 8-dimethyl-10-methylundecane and 2, 2, 4, 4, 6, 6-dimethyl-8-methyl-nonane, sold by Permethyl Corporation. A further example of a hydrocarbon polymer is polybutene, such as the copolymer of isobutylene and butene. A commercially available material of this type is L-14 polybutene from Amoco Chemical Co. (Chicago, Ill., U.S.A.).

Particularly preferred hydrocarbon oils are the various grades of mineral oils. Mineral oils are clear oily liquids obtained from petroleum oil, from which waxes-have been removed, and the more volatile fractions removed by distillation. The fraction distilling between 150° C. to 300° C. is termed mineral oil, and it consists of a mixture of hydrocarbons ranging from $C_8H_{18}$ to $C_2H_{44}$. Suitable commercially available materials of this type include $C_{11}$-$C_{13}$ isoparaffin and Sirius M85 and Sirius M125, all available from Silkolene.

Suitable fatty esters are characterised by having at least 10 carbon atoms, and include esters with hydrocarbyl chains derived from fatty acids or alcohols, e.g., monocarboxylic acid esters, polyhydric alcohol esters, and di- and tricarboxylic acid esters. The hydrocarbyl radicals of the fatty esters hereof can also include or have covalently bonded thereto other compatible functionalities, such as amides and alkoxy moieties, such as ethoxy or ether linkages.

Monocarboxylic acid-esters include esters of alcohols and/or acids of the formula R'COOR in which R' and R independently denote alkyl or alkenyl radicals and the sum of carbon atoms in R' and R is at least 10, preferably at least 20.

Specific examples include, for example, alkyl and alkenyl esters of fatty acids having aliphatic chains with from about 10 to about 22 carbon atoms, and alkyl and/or alkenyl fatty alcohol carboxylic acid esters having an alkyl and/or alkenyl alcohol-derived aliphatic chain with about 10 to about 22 carbon atoms, benzoate esters of fatty alcohols having from about 12 to 20 carbon atoms.

The monocarboxylic acid ester need not necessarily contain at least one chain with at least 10 carbon atoms, so long as the total number of aliphatic chain carbon atoms is at least 10. Examples include isopropyl isostearate, isopropyl myristate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

Di- and trialkyl and alkenyl esters of carboxylic acids can also be used. These include, for example, esters of $C_4$-$C_8$ dicarboxylic acids such as $C_1$-$C_{22}$ esters (preferably $C_1$-$C_6$) of succinic acid, glutaric acid, adipic acid, hexanoic acid, heptanoic acid, and octanoic acid. Examples include diisopropyl adipate, diisohexyl adipate, and diisopropyl sebacate. Other specific examples include isocetyl stearoyl stearate, and tristearyl citrate.

Polyhydric alcohol esters include alkylene glycol esters, for example ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol monostearate, ethoxylated propylene glycol monostearate, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, polyoxyethylene sorbitan fatty acid esters and mono-, di-and triglycerides.

Particularly preferred fatty esters are mono-, di- and triglycerides, more specifically the mono-, di-, and tri-esters of glycerol and long chain carboxylic acids such as $C_1$-$C_{22}$ carboxylic acids. A variety of these types of materials can be obtained from vegetable and animal fats and oils, such as coconut oil, castor oil, safflower oil, sunflower oil, cottonseed oil, corn oil, olive oil, cod liver oil, almond oil, avocado oil, palm oil, sesame oil, peanut oil, lanolin and soybean oil. Synthetic oils include triolein and tristearin glyceryl dilaurate.

Specific examples of preferred materials include cocoa butter, palm stearin, sunflower oil, soybean oil and coconut oil.

The oil may be blended with other materials in the discrete droplets present in compositions according to the invention.

It is preferred that the d(0;5) volume-based median particle diameter of the hydrophobic conditioning oil droplets in the composition is less than 100 micrometers, more preferably less than 40 micrometers, even more preferably less than 12 micrometers and most preferably less than 6 micrometers. Larger particle diameters lead to problems in stabilising the composition from separation of components. Practical difficulties in making emulsion droplets with a median diameter of 0.02 micrometers or less are known to those skilled in the art. Thus it is preferred if the volume-based median diameter d(0.5) is greater than 0.02 micrometers, more preferably greater than 0.03 micrometers, even more preferably greater than 0.1 micrometers. Preferred ranges of median diameter can be formed by combining any of the preferred minimum diameters with any of the preferred maximum diameters.

Volume-based median droplet diameter d(0.5) may be measured by means of a laser light scattering technique, for example using a 2600D Particle Sizer from Malvern Instruments.

The total amount of hydrophobic conditioning oil present in the composition is preferably from 0.1% to 10% by weight of the total composition more preferably from 0.2% to 6%, most preferably 0.5% to 4%.

Silicone Conditioning Oils

Preferred hydrophobic conditioning oils for use in compositions according to the invention are silicones.

Suitable silicones for use as conditioning oils include polydiorganosiloxanes, in particular polydimethylsiloxanes which have the CTFA designation dimethicone. Also suitable for use in compositions of the invention are polydimethyl siloxanes having hydroxyl end groups, which have the CTFA designation dimethiconol.

It is preferred if the silicone oil also comprises a functionalised silicone. Suitable functionalised silicones include, for example, amino-, carboxy-, betaine-, quaternary ammonium-, carbohydrate-, hydroxy- and alkoxy-substituted silicones. Preferably, the functionalised silicone contains multiple substitutions.

For the avoidance of doubt, as regards hydroxyl-substituted silicones, a polydimethylsiloxane merely having hydroxyl end groups (which have the CTFA designation dimethiconol) is not considered a functionalised silicone within the present invention. However, a polydimethylsiloxane having hydroxyl substitutions along the polymer chain is considered a functionalised silicone.

Preferred functionalised silicones are amino-functionalised silicones. Suitable amino functionalised silicones are described in EP 455,185 (Helene Curtis) and include trimethylsilylamodimethicone as depicted below, and are sufficiently water insoluble so as to be useful in compositions of the invention:

$$Si(CH_3)_3—O—[Si(CH_3)_2—O—]_x-[Si(CH_3)(R—NH—CH_2CH_2NH_2)—O—]y -Si (CH_3)_3$$

wherein x+y is a number from about 50 to about 500, and the weight percent amine functionality is in the range of from about 0.03% to about 8% by weight of the molecule, and wherein R is an alkylene group having from 2 to 5 carbon atoms. Preferably, the number x+y is in the range of from about 100 to about 300, and the weight percent amine functionality is in the range of from about 0.03% to 8% by weight of the molecule.

As expressed here, the weight percent amine functionality is measured by titrating a sample of the amino-functionalised silicone against alcoholic hydrochloric acid to the bromocresol green end point. The weight percent amine is calculated using a molecular weight of 45 (corresponding to $CH_3—CH_2—NH_2$).

Suitably, the weight percent amine functionality measured and calculated in this way is in the range from 0.03% to 8%, preferably from 0.5% to 4%.

An example of a commercially available amino-functionalised silicone useful in the silicone component of the composition of the invention is DC-8566 available from Dow Corning (INCI name: dimethyl, methyl (aminoethylaminoisobutyl) siloxane). This has a weight percent amine functionality of about 1.4%.

By "amino functional silicone" is meant a silicone containing at least one primary, secondary or tertiary amine group, or a quaternary ammonium group. Examples of suitable amino functional silicones include: polysiloxanes having the CTFA designation "amodimethicone". Specific examples of amino functional silicones suitable for use in the invention are the aminosilicdne oils DC-8220, DC-8166, DC-8466, and DC-8950-114 (all ex Dow Corning), and GE 1149-75, (ex General Electric Silicones). Suitable quaternary silicone polymers are described in EP-A-0 530 974. A preferred quaternary silicone polymer is K3474, ex Goldschmidt.

Another preferred functional silicone for use as a component in the hydrophobic conditioning oil is an alkoxy-substituted silicone. Such molecules are known as silicone copolyols and have one or more pblyethyleneoxide or polypropyleneoxide groups bonded to the silicone polymer backbone, optionally through an alkyl linking group.

A non-limiting example of a type of silicone copolyol useful in compositions of the invention has a molecular-structure according to the formula depicted below:

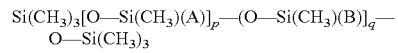

$$Si(CH_3)_3[O—Si(CH_3)(A)]_p—(O—Si(CH_3)(B)]_q—O—Si(CH_3)_3$$

In this formula, A is an alkylene chain with from 1 to 22 carbon atoms, preferably 4 to 18, more preferably 10 to 16. B is a group with the structure: $—(R)-(EO)_r((PO)_s—OH$ wherein R is a linking group, preferably an alkylene group with 1 to 3 carbon atoms. Preferably R is $—(CH_2)_2—$. The mean values of r and s are 5 or more, preferably 10 or more, more preferably 15 or more. It is preferred if the mean values of r and s are 100 or less. In the formula, the value of p is suitably 10 or more, preferably 20 or more, more preferably 50 or more and most preferably 100 or more. The value of q is suitably from 1 to 20 wherein the ratio p/q is preferably 10 or more, more preferably 20 or more. The value of p+q is a number from 11 to 500, preferably from 50 to 300.

Suitable silicone copolyols have an HLB of 10 or less, preferably 7 or less, more preferably 4 or less. A suitable silicone copolyol material is DC5200, known as Lauryl PEG/PPG-18/18 methicone (INCI name), available from Dow Corning.

It is preferred to use a combination of functional and non-functional silicones as the hydrophobic silicone conditioning oil. Preferably the silicones are blended into common droplets prior to incorporation into compositions according to the invention.

The viscosity of the droplets hydrophobic silicone conditioning oil, measured in isolation from the rest of the composition (i.e. not the viscosity of any pre-formed emulsion, but of the hydrophobic conditioning oil itself) is typically from 350 to 200,000,000 $mm^2sec^{-1}$ at 25° C. Preferably the viscosity is at least 5,000 $mm^2sec^{-1}$ at 25° C., more preferably at least 10,000 $mm^2sec^{-1}$. Preferably the viscosity does not exceed 20,000,000 $mm^2sec^{-1}$, more preferably 10,000,000 $mm^2sec^{-1}$, most preferably 5,000,000 $mm^2sec^{-1}$.

Suitable methods for measuring the kinematic viscosity of silicone oils are known to those skilled in the art, e.g. capillary viscometers. For high viscosity silicones, a constant stress rheometer can also be used to measure dynamic viscosity, which is related to kinematic viscosity by the density of the silicone. The viscosity should be measured at low shear rates, less than $10^{-1}$, such that the silicone exhibits Newtonian behaviour (i.e. viscosity independent of shear rate).

It is preferred if silicones are added to the compositions of the invention as pre-formed emulsions with silicone particle diameters as described above generally for hydrophobic conditioning oils. A particularly preferred diameter is from 0.5 to 12 micrometers.

The silicones may be used in combination with volatile silicones. Volatile silicones are short chain or cyclic polydialkyl siloxanes, preferably polydimethylsiloxanes, having a vapour pressure of 10 Pa or more, preferably 100 Pa or more, more preferably 1000 Pa or more at 25° C.

Hydrophobically Modified Clay

The compositions of the invention preferably comprise hydrophobically modified clay in an amount of from 0.01% to 5% by weight, preferably from 0.01% to 3% by weight, more preferably from 0.05% to 1% by weight based on the total weight of the composition. Higher levels of hydrophobically modified clays can give unpleasant tactile properties to the composition for some consumers.

Hydrophobically modified clays may be used in the present invention either singly or in combination with one or more other hydrophobically modified clays.

Suitable clays include hydrophobically modified natural clays and synthetic clays. In general, the term clay refers to a composition comprising particles which have a net electrostatic (i.e. positive or negative charge) on at least one surface.

Preferably, the hydrophobically modified clay has a layered structure. In the compositions of the invention, the hydrophobically modified clay is advantageously present in the form of a dispersion or suspension of the clay particles.

Hydrophobically modified clays of the invention may be anionic or cationic, ie, they may have a net charge on the surface of the clay that is negative or positive, respectively. The term anionic clays and related terms, as used herein, refers to clays which are themselves anionic in nature i.e., the clays themselves are negatively charged at their surface and are capable of exchanging cations. Similarly, the term cationic clays and related terms, as used herein, refers to clays which are themselves cationic in nature i.e., the clays themselves are positively charged at their surface and are capable of exchanging anions.

Hydrophobically modified clays are derivable from clays by modification of the clay with a hydrophobic material.

Preferred anionic clays are clays from the smectite class of clays. Typically, clays of this type are crystalline, expandable, three-layer clays.

Smectite clays are, for example, disclosed in U.S. Pat. Nos. 3,862,058, 3,948,790, 3,954,632 and 4,062,647 and in EP-A-299,575 and EP-A-313,146, all in the name of Procter & Gamble Company.

The term smectite clays herein includes both the clays in which aluminium oxide is present in a silicate lattice and the clays in which magnesium oxide is present in a silicate lattice. Typical smectite clay compounds include the compounds having the general formula $Al_2(Si_2O_5)_2(OH)_2.nH_2O$ and the compounds having the general formula $Mg_3(Si_2O_5)_2(OH)_2.nH_2O$, and derivatives thereof, for example in which a proportion of the aluminium ions are replaced with magnesium ions or a proportion of the magnesium ions are replaced with lithium ions and/or some of the hydroxyl ions are replaced by fluoride ions; the derivatives may comprise a further metal ion to balance the overall charge. Smectite clays tend to adopt an expandable, three-layer structure.

The hydrophobically modified clay is preferably an expandable three-layer clay comprising at least 75% by weight of the clay of atoms selected from oxygen, silicon and aluminium and/or magnesium. More preferably, the hydrophobically modified clay comprises atoms selected from oxygen, silicon and aluminium and/or magnesium in an amount of at least 5% by weight of the clay, for each of the atoms.

Specific examples of suitable smectite clays include those selected from the classes of the montmorillonites, hectorites, volchonskoites, nontronites, saponites, beidelites and sauconites, particularly those having an alkali or alkaline earth metal ion within the crystal lattice structure. Particularly preferred are hectorites, montmorillonites, nontronites, saponites, beidelites, sauconites and mixtures thereof. Preferred are montmorillonites, e.g., bentonites and hectorites, with bentonites being particularly preferred.

The hydrophobically modified clay is preferably a hydrophobically treated bentonite clay.

It is customary to measure cation exchange capacity (sometimes termed "base exchange capacity") in terms of milliequivalents per 100 g of clay (meq/100 g). The cation exchange capacity of clays can be measured in several ways, including by electrodialysis, by exchange with ammonium ion followed by titration or by a methylene blue procedure, all as fully set fourth in Grimshaw, "The Chemistry and Physics of Clays", pp. 264-265, Interscience (1971). The cation exchange capacity of a clay mineral relates to such factors as the expandable properties of the clay and the charge of the clay, which, in turn, is determined at least in part by the lattice structure, and the like.

Preferred anionic clays for use in the present invention have an ion exchange capacity of from 0.7 meq/100 g to 150 meq/100 g. Particularly preferred are clays having an ion exchange capacity of from 30 meq/100 g to 100 meq/100 g.

The clays preferably have an average particle size in the range of from 0.0001 µm to 800 µm, more preferably from 0.01 µm to 400 µm such as from 0.02 µm to 220 µm, even more preferably 0.02 µm to 100 µm. Particle sizes can be determined using a Malvern Mastersizer (Malvern Instruments, UK).

The hydrophobically modified clays used in the compositions of the invention preferably have organic ions replacing at least a proportion of inorganic metal ions by ion exchange processes known in the art. Preferably, the clay is hydrophobically modified by exchange into the clay of cations comprising one or more alkyl groups containing from 6 to 30 carbon atoms. The cationic group is preferably a quaternary ammonium group. Advantageously, the cations have the formula $N^+R^1R^2R^3R^4$ wherein $R^1$, $R^2$, $R^3$ and $R^4$ are independently ($C_1$ to $C_{30}$) alkyl, preferably ($C_6$ to $C_{30}$) alkyl, or benzyl. Preferably, one, two or three of $R^1$, $R^2$, $R^3$ and $R^4$ are independently ($C_6$ to $C_{30}$) alkyl and the other $R^1$, $R^2$, $R^3$ and $R^4$ group or groups are ($C_1$-$C_6$) alkyl or benzyl. Suitably, two of $R^1$, $R^2$, $R^3$ and $R^4$ are independently ($C_6$ to $C_{30}$) alkyl and the other $R^1$, $R^2$, $R^3$ and $R^4$ groups are ($C_1$-$C_6$) alkyl or benzyl optionally, the alkyl groups may comprise one or more ester (—OCO— or —COO—) and/or ether (—O—) linkages within the alkyl chain. Alkyl groups may be straight chain or branched and, for alkyl groups having 3 or more carbon atoms, cyclic. The alkyl groups may be saturated or may contain one or more carbon-carbon double bonds (e.g., oleyl). The alkyl groups are optionally substituted with one or more hydroxyl groups. Alkyl groups are optionally ethoxylated with one or more ethyleneoxy groups on the alkyl chain. Preferably, the alkyl groups are straight chain, saturated groups.

Preferred compounds of formula $N^+R^1R^2R^3R^4$ which have two ($C_6$ to $C_{30}$) alkyl groups include: cetyl, stearyl and dibehenyl trimethylammonium chloride.

Preferred compounds of formula $N^+R^1R^2R^3R^4$ which have two ($C_6$ to $C_{30}$) alkyl groups include:

Distearyldimethylammonium chloride (distearyl dimonium chloride);
Distearyldimethylammonium bromide (distearyl dimonium bromide);
Dicetyldimethylammonium chloride (dicetyl dimonium chloride);
Dicetyldimethylammonium bromide (dicetyl dimonium bromide);
Dimethyldi(hydrogenated tallow) ammonium chloride (Quaternium-18);
Dicetylmethylbenzylammonium chloride;
Dicocodimethylammonium chloride (dicoco dimonium chloride);
Dicocodimethylammonium bromide (dicoco dimonium bromide);
Dibehenyl/diarachidyldimethylammonium bromide (dibehenyl/diarachidyl dimonium bromide);
Dibehenyl/diarachidyldimethylammonium chloride (dibehenyl/diarachidyl dimonium chloride);
Dibehenyl dimonium methyl sulfate (dibehenyl dimonium methyl sulfate);
Hydroxypropyl bis-stearylammonium chloride (hydroxypropyl bis-stearyl dimonium chloride);
Dibehenyldimethylammonium chloride (dibehenyl dimonium chloride);
Dibehenylmethylbenzylammonium chloride;
Dimyristyldimethylammonium chloride (dimyristyl dimonium chloride); and
Dimyristyldimethylammonium bromide (dimyristyl dimonium bromide).

Preferred compounds of formula $N^+R^1R^2R^3R^4$ which have three ($C_6$ to $C_{30}$) alkyl groups include compounds which have three alkyl groups having 8 to 22 carbon atoms and one alkyl group having 1 to 4 carbon atoms, such as, for example:
Tricetylmethylammonium chloride.
Tricetylmethylammonium bromide;
Tricetylmethylammonium methylsulfate;
Tri(($C_8$-$C_{10}$) alkyl)methylammonium chloride;
Tri(($C_8$-$C_{10}$) alkyl)methylammonium bromide; and
Tri(($C_8$-$C_{10}$) alkyl)methylammonium methylsulfate.

A particularly preferred material is bentonite modified with Quaternium-18 (ie, di-hydrogenated tallow dimethyl ammonium cations). An example of such a product is Tixogel MP 100™ from Sud Chemie. Other suitable hydrophobically modified clays include Quaternium benzalkonium bentonite, Quaternium-18 hectorite, stearalkonium bentonite, stearalkonium hectorite and dihydrogenated tallow benzylmonium hectorite.

Mousses

Hair treatment compositions in accordance with the invention may also take the form of aerosol foams (mousses) in which case a propellant must be included in the composition. This agent is responsible for expelling the other materials from the container and forming the hair mousse character.

The propellant gas can be any liquefiable gas conventionally used for aerosol containers. Examples of suitable propellants include dimethyl ether, propane, n-butane and isobutane, used singly or in admixture.

The amount of the propellant gases is governed by normal factors well known in the aerosol art. For hair mousses, the level of propellant is generally from 3 to 30, preferably from 5 to 15-percent by weight of the total composition.

Optional Ingredients

Compositions of this invention may contain any other ingredient normally used in hair treatment formulations. These other ingredients may include viscosity modifiers, preservatives, colouring agents, polyols such as glycerine and polypropylene glycol, chelating agents such as EDTA, antioxidants, fragrances, antimicrobials and sunscreens. Each of these ingredients will be present in an amount effective to accomplish its purpose. Generally these optional ingredients are included individually at a level of up to 5 percent by weight of the total composition.

Preferably, compositions of this invention also contain adjuvants suitable for hair care. Generally such ingredients are included individually at a level of up to 2, preferably up to 1 percent by weight of the total composition.

Among suitable hair care adjuvants, are:

(i) natural hair root nutrients, such as amino acids and sugars. Examples of suitable amino acids include arginine, cysteine, glutamine, glutamic acid, isoleucine, leucine, methionine, serine and valine, and/or precursors and derivatives thereof. The amino acids may be added singly, in mixtures, or in the form of peptides, e.g. di- and tripeptides. The amino acids may also be added in the form of a protein hydrolysate, such as a keratin or collagen hydrolysate. Suitable sugars are glucose, dextrose and fructose. These may be added singly or in the form of, e.g. fruit extracts. A particularly preferred combination of natural hair root nutrients for inclusion in compositions of the invention is isoleucine and glucose. A particularly preferred amino acid nutrient is arginine.

(ii) hair fibre benefit agents. Examples are ceramides, for moisturising the fibre and maintaining cuticle integrity. Ceramides are available by extraction from natural sources, or as synthetic ceramides and pseudoceramides. A preferred ceramide is Ceramide II, ex Quest. Mixtures of ceramides may also be suitable, such as Ceramides LS, ex Laboratoires Serobiologiques.

The invention will now be illustrated by the following non-limiting Examples, in which Examples of the invention are indicated by a number and Comparative Examples are indicated by a letter.

| Component | Example 1 | Example A |
|---|---|---|
| Cetrimonium chloride | 1.2 | 1.2 |
| Dibehenyl imidazoline quat (Quaternium-91) | 0.25 | 0.25 |
| Cetrimonium methosulphate | 0.1 | 0.1 |
| Hydroxyethyl cetyldimonium phosphate (LUVIQUAT mono CP ex BASF) | 0.025 | 0.0 |
| Natrosol | 0.1 | 0.1 |
| Cetearyl alcohol | 4.15 | 4.15 |
| Cetyl alcohol | 1.00 | 1.00 |
| DC1785 | 2.0 | 2.0 |
| DC245 | 2.0 | 2.0 |
| Water and minors | to 100 | to 100 |

Example 1 gave better conditioning and feel when applied to the hair than comparative Example A.

The invention claimed is:

1. A hair treatment composition consisting of i) a surfactant wherein the surfactant system consists of:
   a) from 0.2 to 5% by weight of a mixture of cetrimonium chloride and cetrimonium methosulfate
   b) from 0.01 to 1.0% by weight of dibehenyl imidazline quat
   c) from 0.0001 to 0.5% by weight of hydroxy ethyl cetyldimonium phosphate
   ii) 1 to 10% by weight of a mixture of cetearyl alcohol and cetyl alcohol
   iii) 0.1 to 10% by weight of cyclopentasiloxane and mixture of dimethiconol and dodecyl benzene sulfonate
   iv) 0.1% by weight of hydroxyethyl cellulose
   v) water and minors to 100% by wt %.

2. A hair treatment composition according to claim 1 in which the level of a) is from 0.3 to 5 wt % of the total composition.

3. A hair treatment composition according to claim 1 in which the b) is from 0.05 to 0.5% by weight of the total composition.

4. A hair treatment composition according to claim 1 in which c) is from 0.001 to 0.2% by weight of the total composition.

5. A method of conditioning the hair comprising the step of applying to the hair and/or scalp a composition according to claim 1.

* * * * *